(12) United States Patent
Yang et al.

(10) Patent No.: US 12,239,746 B2
(45) Date of Patent: Mar. 4, 2025

(54) SUPERABSORBENT MATERIAL ABSORBENT CAPACITY INCREASE WITH USE OF MULTIFUNCTIONAL CHEMICAL AGENTS

(71) Applicant: Kimberly-Clark Worldwide, Inc., Neenah, WI (US)

(72) Inventors: Kaiyuan Yang, Cumming, GA (US); Xuedong Song, Alpharetta, GA (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 398 days.

(21) Appl. No.: 17/642,283

(22) PCT Filed: Oct. 23, 2019

(86) PCT No.: PCT/US2019/057678
§ 371 (c)(1),
(2) Date: Mar. 11, 2022

(87) PCT Pub. No.: WO2021/080583
PCT Pub. Date: Apr. 29, 2021

(65) Prior Publication Data
US 2022/0296767 A1 Sep. 22, 2022

(51) Int. Cl.
| | |
|---|---|
| *A61L 15/20* | (2006.01) |
| *A61L 15/60* | (2006.01) |
| *B01J 20/26* | (2006.01) |
| *C07C 229/08* | (2006.01) |
| *C07C 279/02* | (2006.01) |
| *C07C 279/14* | (2006.01) |
| *C08F 20/06* | (2006.01) |

(52) U.S. Cl.
CPC ............... *A61L 15/20* (2013.01); *A61L 15/60* (2013.01); *B01J 20/265* (2013.01); *C07C 229/08* (2013.01); *C07C 279/02* (2013.01); *C07C 279/14* (2013.01); *C08F 20/06* (2013.01)

(58) Field of Classification Search
CPC ........ A61L 15/20; A61L 15/60; B01J 20/265; C07C 229/08; C07C 279/02; C07C 279/14; C08F 20/06
USPC ..................................................... 525/329.9
See application file for complete search history.

(56) References Cited

U.S. PATENT DOCUMENTS

| | | | |
|---|---|---|---|
| 4,654,039 A | 3/1987 | Brandt et al. | |
| 4,766,173 A | 8/1988 | Bailey et al. | |
| 5,247,068 A | 9/1993 | Donachy et al. | |
| 5,955,549 A | 9/1999 | Chang et al. | |
| 5,998,032 A | 12/1999 | Hansen et al. | |
| 6,387,495 B1 | 5/2002 | Reeves et al. | |
| 6,855,434 B2 | 2/2005 | Romans-Hess et al. | |
| 7,144,474 B1 | 12/2006 | Hansen et al. | |
| 7,265,257 B2 | 9/2007 | Baldwin et al. | |
| 7,642,397 B2 | 1/2010 | Cohen et al. | |
| 8,137,746 B2 | 3/2012 | Schmidt et al. | |
| 8,791,320 B2 | 7/2014 | Ehrnsperger et al. | |
| 2002/0164375 A1 | 11/2002 | Hansen et al. | |
| 2003/0162869 A1 | 8/2003 | Romans-Hess et al. | |
| 2010/0035757 A1 | 2/2010 | Furno et al. | |
| 2011/0123604 A1 | 5/2011 | Strickland et al. | |

FOREIGN PATENT DOCUMENTS

| | | |
|---|---|---|
| CN | 103547603 A | 1/2014 |
| CN | 104039847 A | 9/2014 |
| CN | 105392805 A | 3/2016 |
| EP | 0441975 A1 | 8/1991 |
| JP | H10859820 A | 3/1996 |
| JP | 2002282687 A | 10/2002 |
| WO | 9320856 A1 | 10/1993 |
| WO | 9510543 A1 | 4/1995 |
| WO | 03041752 A1 | 5/2003 |
| WO | 03072153 A2 | 9/2003 |
| WO | 2009029841 A1 | 3/2009 |

OTHER PUBLICATIONS

Office Action for Brazil Patent Application No. BR112022005344-4 dated May 2, 2023; 4 pp.
First Office Action for Chinese Patent Application No. 201980100644.9 dated Mar. 1, 2023; 12 pp.
Second Office Action for Chinese Patent Application No. 201980100644.9 dated Aug. 9, 2023; 15 pp.
PCT International Search Report and Written Opinion for Patent Application PCT/US2019/057678 mailed Feb. 28, 2020; 12 pp.
Buchholz, Fred L. et al., "Modern Superabsorbent Polymer Technology," Nov. 1997; Chapter 7, Section 7.1; pp. 251-258.
Third Party Observations received for Patent Application PCT/US2019057678 submitted Feb. 15, 2022; 9 pp.
Finn, Niall et al., "Electrospun Poly(Acrylic Acid)/Lysine Fibers and the Interactive Effects of Moisture, Heat, and Cross-Link Density on their Behavior," Journal of Applied Polymer Science, vol. 132, Issue 2; Aug. 13, 2014; 2 pp.
Tamatani, H. et al., "Superabsorbent Polymers Synthesized from Amino Acids," Proceedings of the 53rd Annual Technical Conference; Boston, MA; 1995, vol. 2; pp. 1510-1513.
Office Action received for BR 112022005344 on Aug. 13, 2024; 15 pps.

*Primary Examiner* — Edward M Johnson
(74) *Attorney, Agent, or Firm* — Armstrong Teasdale LLP (57) ABSTRACT

A method for increasing absorbent capacity of a superabsorbent material (SAM) by treating the SAM with a selected multifunctional chemical agent (MCA) or a combination of a plurality of selected MCAs is described herein. The selected MCA(s) may interact with the polymer chain of the SAM through one or a plurality of mechanisms that enhance the absorbent capacity of the SAM. In various preferred embodiments, SAMs include polyelectrolytes that are made from polymerizing mixtures of acrylic acid monomer and acrylic acid sodium salt, and L-arginine or lysine is selected as the MCA.

4 Claims, 5 Drawing Sheets

SUPERABSORBENT MATERIAL ABSORBENT CAPACITY INCREASE WITH USE OF MULTIFUNCTIONAL CHEMICAL AGENTS

BACKGROUND OF THE DISCLOSURE

Superabsorbent materials (SAM) have been developed in recent years that are capable of absorbing many times their own weight of liquid. SAM, also known as water insoluble hydrogels, are polymer materials that have been used to increase the absorbency of sanitary products such as diapers and incontinence pads and underwear. SAM are often provided in the form of particulate powders, granules, or fibers that are distributed throughout absorbent cellulosic products to increase the absorbency of the product. Superabsorbent particles are described, for example, in U.S. Pat. Nos. 4,160,059; 4,676,784; 4,673,402; 5,002,814; and 5,057,166. Products such as diapers that incorporate absorbent hydrogels are shown in U.S. Pat. Nos. 3,669,103 and 3,670,731.

More specifically, ionic gel-based superabsorbents, or polyelectrolytes, have widely been used in personal care products. They are special because of their unique abilities of absorbing water-containing liquids. The dramatic absorbing and swelling powers of these materials stem from both the electrostatic repulsion between the negative charges on the polymer backbone such as a carboxylate —COO⁻ and the osmotic pressure of the counter positive ions such as sodium $Na^+$.

However, the water absorbing and swelling powers of ionic superabsorbents may be greatly reduced in salt-containing solutions such as physiological fluids like urine and blood. The reason for this salt-sensitivity is that the excessive ions such as sodium ions ($Na^+$) in physiological fluids may effectively screen the polymer backbone charges, which may lead to reduced counter ion numbers and repulsion forces and thus less swelling. In some cases, the absorbing and swelling powers may be lost fully as the ionic gels may be screened to non-ionic gels. Therefore, in order to compensate for the salt-sensitivity of SAMs, more SAM is used in absorbent articles. The use of more SAM may result in bulkier absorbent articles, uncomfortable user experiences and higher product costs. Accordingly, there is still a need to improve the absorbent capacity of SAM.

SUMMARY OF THE DISCLOSURE

The present invention is directed to a method of increasing the absorbent capacity of a superabsorbent material (SAM) by treating the SAM with a selected multifunctional chemical agent (MCA) or combinations of such selected MCAs. The MCAs may be illustrated as a tetrahedron compound with four different functional groups as shown in Formula (I):

(I)

The X group on Formula (I) includes —COOH, —SO₃H, —OSO₃H or similar structures thereof. Adjacent to the X group on Formula (I) is a $NR_1R_2$ group. The N in the $NR_1R_2$ group may be selected from a primary, secondary and tertiary amino group and the $R_1$ and $R_2$, groups may be selected from —H, -Me, -Et, and -Bu. The $R_3$ group on Formula (I) is selected from —H, -Me, -Et, or -Bu. The $R_3$ group is preferably —H and -Me.

The $R_4$ group of Formula (I) is an alkyl chain of eight or fewer carbons. The $R_4$ group also includes at least one or a plurality of additional primary, secondary or tertiary amino groups that are attached to any one of the carbons on the alkyl chain. Further, each carbon on the alkyl chain includes an additional substituent group. Each of these additional substituent groups may be selected from one of the following substituents: —H, -Me, -Et, or -Bu. Alternatively, each of these additional substituent groups may be selected from nitrogen-containing alkyl groups.

DEFINITIONS

When introducing elements of the present disclosure or the preferred embodiment(s) thereof, the articles "a", "an", and "the" when used herein are intended to mean that there are one or more of the elements.

The terms "comprising", "including" and "having" when used herein are intended to be inclusive and mean that there may be additional elements other than the listed elements.

The term "superabsorbent material" or "SAM" when used herein refers to a superabsorbent polymer which may absorb and retain extremely large amounts of a liquid relative to its own mass. A SAM's ability to absorb water depends on the ionic concentration of the aqueous solution such as urine, blood or other body exudates.

The term "absorbent article" when used herein refers to devices that absorb and contain body exudates, and, more specifically, refers to devices that are placed against or in proximity to the body of the wearer to absorb and contain the various exudates discharged from the body. Absorbent articles may include diapers, pant diapers, open diapers, diaper covers having fastening means for fastening the diaper, training pants, adult incontinence undergarments, feminine hygiene products, breast pads, care mats, bibs, wound dressing products, and the like. As used herein, the term "body exudates" includes, but is not limited to, urine, blood, vaginal discharges, breast milk, sweat and fecal matter.

The term "secondary dissociation" when used herein refers to a charged or non charged chemical fragment formed after the selected multifunctional chemical agents interact with the SAM (e.g. bulky ions) from which a mono counter ion may further dissociate to become a fully dissociated free ion which will further help to increase the SAM's osmotic pressure and thus swelling.

The term "superabsorbent particle," when used herein refers to the form of discrete units. The discrete units may comprise flakes, fibers, agglomerates, granules, powders, spheres, pulverized materials, or the like, as well as combinations thereof. The superabsorbent material particles may have any desired shape: for example, cubic, rod like polyhedral, spherical or semi-spherical, rounded or semi-rounded, angular, irregular, et cetera.

DETAILED DESCRIPTION

Superabsorbent materials (SAMs) are well known to be very sensitive to salt screening during swelling in aqueous solutions such as urine. Accordingly, various attempts have been made to mitigate or manage salt sensitivity but most of these attempts are either not practical or cost effective. Therefore, it was surprisingly and unexpectedly found that by treating a SAM with a selected multifunctional chemical agent (MCA) or combinations of such selected multifunctional chemical agents (MCA) may significantly increase the SAM's absorbent capacity. More specifically, neutral MCAs have been found to provide a significant increase in absorbent capacity when used to treat SAM.

SAM being treated with a selected MCA include polyelectrolytes that generally consist of repeated units of negative:positive ion pairs along their polymer chains (e.g. carboxylates, phosphates, sulfates, sulfonates and similar structures thereof). For example, SAM used in the present invention are polyelectrolytes that are made from polymerizing mixtures of acrylic acid monomer and acrylic acid sodium salt at a 30% to 70% ratio. However, the polymerizing mixtures of acrylic acid monomer and acrylic acid sodium salt may be described at any desired percent ratio.

In one aspect of the invention, the selected MCA disclosed herein for treating SAM may be used by itself or may be combined with one or more additional selected MCAs so that the maximum absorbent capacity increases may be achieved. More specifically, the selected MCA(s) for treating SAM for absorbent capacity increases are generally categorized into a structural formula, Formula (I).

In an embodiment of the present invention, the selected MCAs for treating SAM for capacity increases are generally described to have a tetrahedron structure with four different functional groups as set forth in Formula (I):

(I)

The X group on Formula (I) may be an acid or neutral functionality group. The term neutral when used herein refers to a chemical agent or structure of Formula (I) that has a pH from 6.5 to 7.5. More specifically, the X group includes —COOH, —SO$_3$H, —OSO$_3$H or similar structures thereof. Adjacent to the X group on Formula (I) is a NR$_1$R$_2$ group. The N in the NR$_1$R$_2$ group is selected from a primary, secondary and tertiary amino group and the R$_1$ and R$_2$, groups are selected from —H, -Me, -Et, and -Bu. The NR$_1$R$_2$ group may form internal zwitterionic structures with its acid group thereby producing more counterions and thus more greatly enhancing the absorbent capacity of SAM.

The R$_3$ group as shown in Formula (I) includes one of the following substituents: —H, -Me, -Et, or -Bu. The substituents —H and -Me are preferable to use in the R$_3$ group position. The choice for using theses substituents for the R$_3$ group is because these substituents are less sterically bulky for MCAs to access the SAM polymer chains.

The R$_4$ group as shown in Formula (I) includes an alkyl chain that has eight or fewer carbons. Further, the R$_4$ group includes at least one or more additional primary, secondary or tertiary amino groups that are attached to any one of the carbons on the alkyl chain. Each carbon on the alkyl chain includes its own additional substituent groups and each of these additional substituent groups may be selected from one of the following substituents: —H, -Me, -Et, or -Bu. Or, these additional substituent groups may be selected from nitrogen-containing alkyl groups. The nitrogen may be attached to one or a plurality of alkyl groups.

The amino group on the alkyl chain may either freely coordinate to the counter sodium ions of acrylate-Na ion pair units along the SAM polymer chain or the amino group may function as a base that may deprotonate the weak acid like un-neutralized acrylic acid units along the SAM polymer chains.

In an aspect of the invention, the SAM treated by selected MCA(s) may be a polyacrylate-based material. The polyacrylate-based material includes acrylate sodium and un-neutralized acrylic acid. The acrylate sodium includes about 50-100% and the un-neutralized acrylic acid includes about 0-50% of the total polyacrylate-based material. Alternatively, the SAM treated by selected MCA(s) may be a surface cross-linked material. The surface cross-linked material has a size range from about 50 to about 1000 microns.

In a further aspect of the present invention, the selected MCA may be used to treat SAM after the SAM has been prepared. In another aspect of the invention, one or more selected MCAs may be combined with prepared SAM. As a result, the selected MCAs will start to interact with the SAM polymer chains immediately when the mixed SAM and selected MCAs contact a swelling liquid such as urine or other bodily exudates. In another aspect, a selected MCA may be introduced into a pre-made sample of SAM during a surface cross-linking step that occurs during SAM manufacturing. In yet a further aspect of the invention, the selected MCA may be introduced in an initial polymerization step of SAM manufacturing so that the interactions between selected and polymer chains may be fully accessed.

In another aspect of the invention, a selected MCA may be combined with one or more selected MCAs or a plurality of MCAs so that the maximum absorbent capacity increases may be achieved. Accordingly, in an embodiment of the invention, the amount of MCA(s) used for treating SAM may be controlled so as not to exceed 25% of the total weight of the SAM. Excessive weight loading of selected MCA(s) may not be desirable as it may not only saturate the SAM interaction sites, but also increase the chances that selected MCA(s) may become a cross-linking agent, which will lead to lowered absorbent capacity due to reduced polymer chain flexibility. Additionally, excessive weight loading of selected MCA(s) may be cost prohibitive and it will not be an efficient pathway for absorbent capacity increases. In an additional aspect of the invention, enhancing the SAM's absorbent capacity with the selected MCAs of Formula (I) may be accomplished by at least one or a combination of a plurality of the following mechanisms:
- a) forming complexes with the SAM's counter ions which may pull away from the polymer chain;
- b) deprotonating an un-neutralized acrylic acid group by one or more selected MCA's amino groups;
- c) secondary dissociating from big ions formed after interactions between SAM's ion pairs and selected MCAs;
- d) bulky ions forming from interactions between SAM chain ion pairs and selected MCA(s). The bulky ion formation may decrease the charge density of the counter ions so that their tendency to bind with a polymer chain may be reduced;
- e) ion-exchanging between ion pairs on a SAM's polymer chain and selected MCA(s) so that more counter ions may be added to the polymer chain; and
- f) forcing charge-charge separation after forming big ions which may occur after interactions between the SAM's ion pairs and selected MCA(s). Forced charge-charge separation may increase polymer chain negative charge density and thus charge-charge repulsion along the polymer chain for increased swelling.

Figure 1:
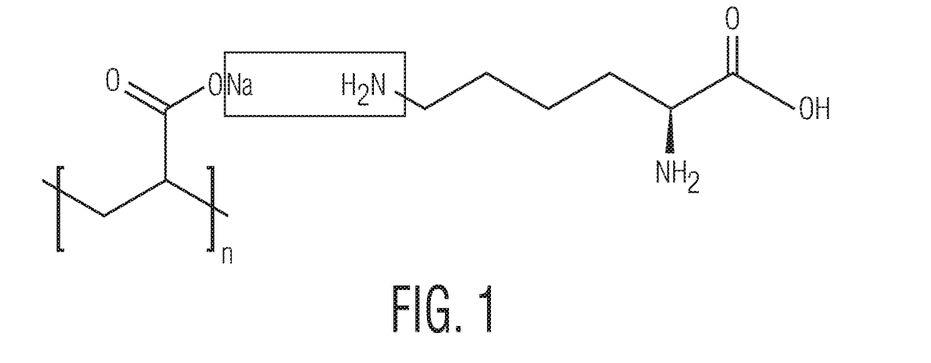
FIG. 1 shows that an amino group on an $R_4$ group forms a complex with sodium counter ions along the SAM's acrylate sodium ion pairs whereby the sodium ion pairs pull away from the SAM polymer chains.
Figure 2:
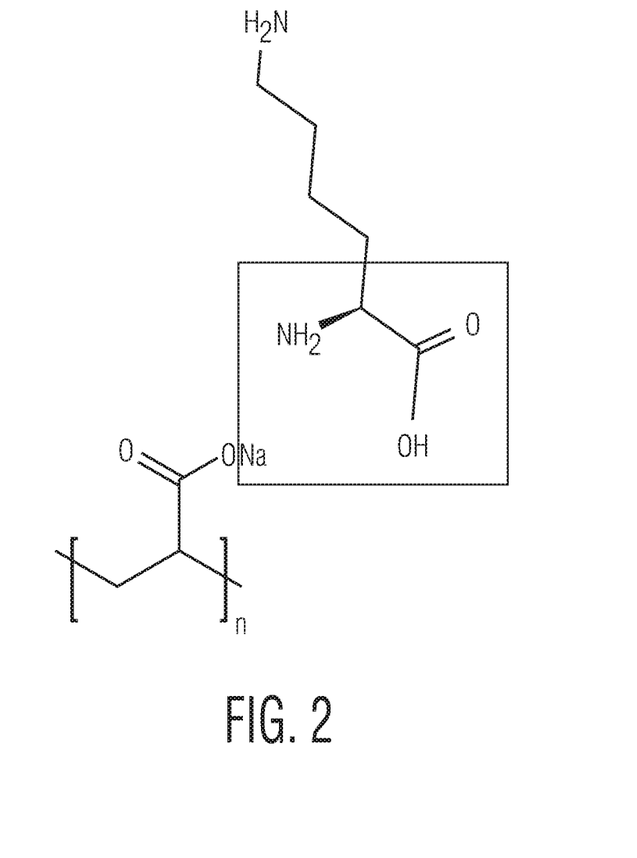
FIG. 2 shows that an acid functionality of a selected MCA forms a complex with sodium counter ions whereby the sodium ion pairs pull away from the SAM polymer chains.

In view of the above absorbent capacity enhancement mechanisms, FIGS. 1-5 show these mechanisms through various structural interactions. For example, FIG. 1 shows that an amino group on an $R_4$ group forms a complex with sodium counter ions along the SAM's acrylate sodium ion pairs whereby the sodium ion pairs pull away from the SAM polymer chains. FIG. 2 shows a functional group of a selected MCA that may form bulky ions after deprotonating un-neutralized acrylic acid units. The formation of bulky ions may force charge-charge separation between a polymer chain and its counter ions.

Figure 3:
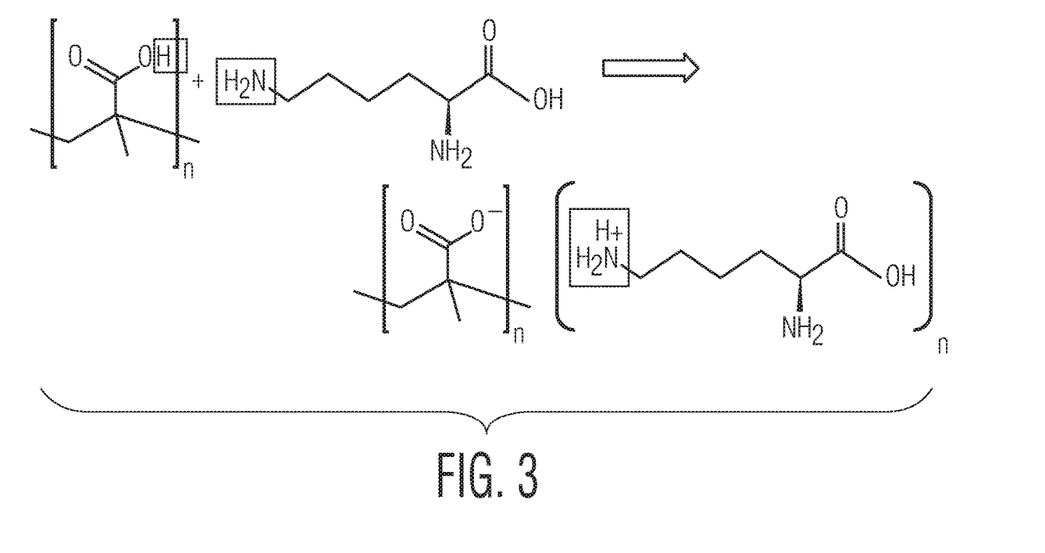
FIG. 3 shows the formation of a big bulky counter ion after deprotonation of a SAM's un-neutralized acrylic acid units by selected MCAs.
Figure 4:
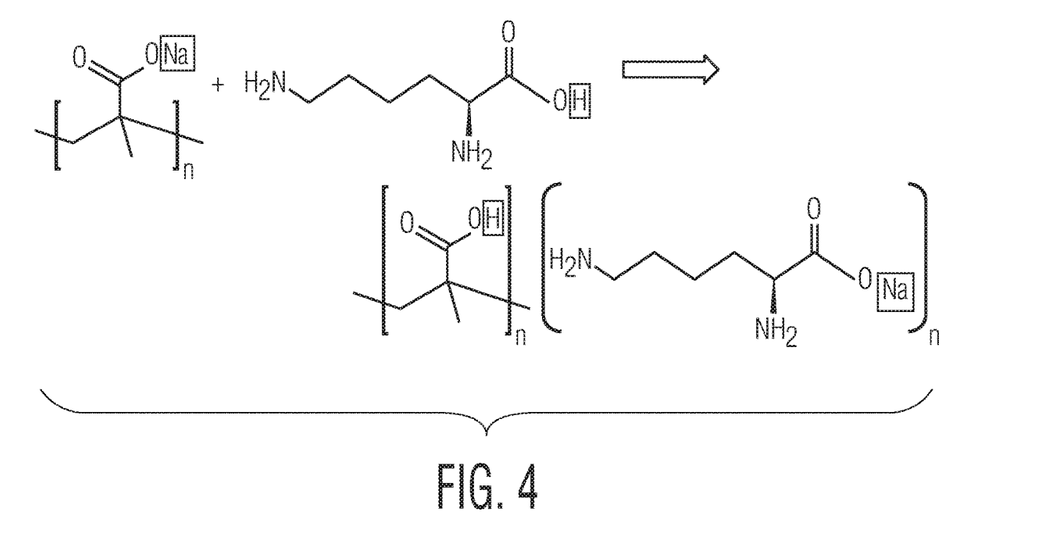
FIG. 4 shows the repositioning of a sodium ion away from SAM's polymer chain by ion-exchange between acid functionality of a selected MCA and a SAM's counter ions of acrylate sodium ion pairs.
Figure 5:
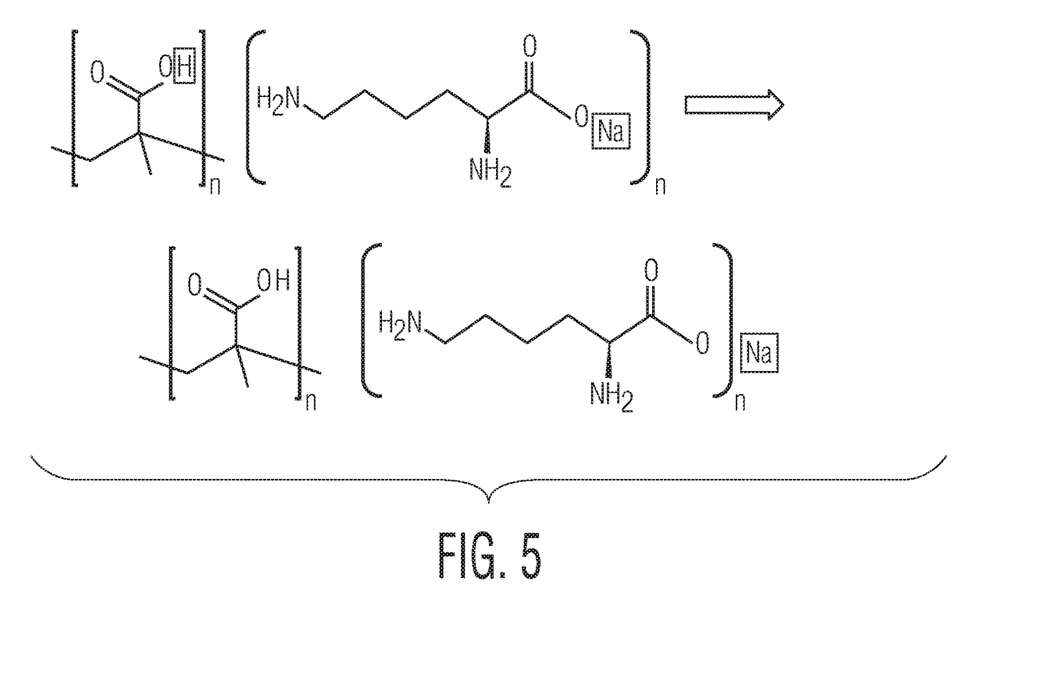
FIG. 5 shows secondary dissociations from bulky ions to allow more free counter ions.

FIG. 3 shows the formation of a big bulky counter ion after deprotonation of a SAM's un-neutralized acrylic acid units by selected MCAs. FIG. 4 shows the repositioning of a sodium ion away from the SAM's polymer chain by ion-exchange between acid functionality of a selected MCA and a SAM's counter ions of acrylate sodium ion pairs. FIG. 5 shows secondary dissociations from bulky ions to allow more free counter ions.

Figure 6:
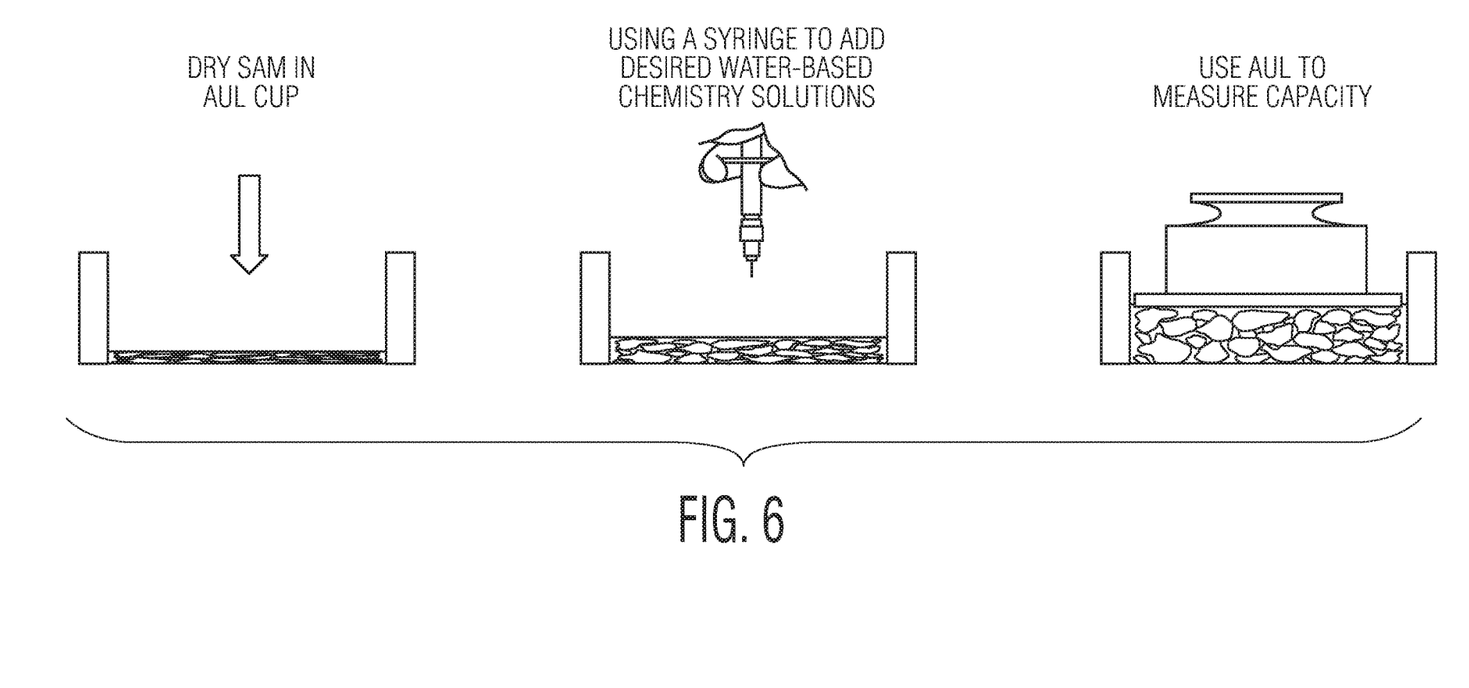
FIG. 6 is a schematic view of a forced fluid distribution by treating the SAM in an absorbent article with selected MCAs to form desired zones of increasing and decreasing absorbent capacity.

In another aspect of the present invention, the discovery of selected MCA(s) for SAM absorbent capacity increases will allow a personal care manufacturer to use one SAM to produce an absorbent article (i.e. diaper) with different absorbent capacity zones for forced fluid redistribution. For example, as shown in FIG. 6, capacity-enhancing MCA(s) such as described in this invention may be applied to desired areas on an absorbent article that may require higher absorbent capacity for leak prevention while MCA(s) with lower absorbent capacity may be applied to areas into which excess urine may be redistributed. Such forced fluid redistribution may improve the absorbent article wearer's comfort and potentially skin dryness.

To further demonstrate the uniqueness of the selected MCA(s) of Formula (I), various other MCA(s) have been tested under the same testing conditions and were found to significantly decrease the absorbent capacity. Please see tables 3-5.

Test Methods
Absorbent Capacity

The absorbent capacity of SAM may be measured using an Absorbency Under Load ("AUL") test, which is a well-known test for measuring the ability of superabsorbent particles to absorb a 0.9 wt. % solution of sodium chloride in distilled water at room temperature (test solution) while the particles are under a load. For example, 0.16 grams of superabsorbent particles may be confined within a 5.07 $cm^2$ area of an Absorbency Under Load ("AUL") cylinder under a nominal pressure of 0.01 psi, 0.3 psi, 0.6 psi or 0.9 psi. The sample is allowed to absorb the test solution from a dish containing excess fluid. At predetermined time intervals, a sample is weighed after a vacuum apparatus has removed any excess interstitial fluid within the cylinder. This weight versus time data is then used to determine the Absorption Rates at various time intervals.

The AUL test apparatus is measured according to EDANA recommended test method WSP 242.3 which is similar to a GATS (gravimetric absorbency test system), available from M/K Systems, as well as the system described by Lichstein at pages 129-142 of the INDA Technological Symposium Proceedings, March 1974. A ported disk is also utilized having ports confined within a 2.5-centimeter diameter area. The resultant AUL is stated as grams of liquid retained per gram weight of the sample (g/g).

To carry out the test, the following steps may be performed:
- (1) Wipe the inside of the AUL cylinder with an anti-static cloth, and weigh the cylinder, weight and piston;
- (2) Record the weight as CONTAINER WEIGHT in grams to the nearest milligram;
- (3) Slowly pour the 0.16±0.005 gram sample of the superabsorbent particles into the cylinder so that the particles do not make contact with the sides of the cylinder or it can adhere to the walls of the AUL cylinder;
- (4) Weigh the cylinder, weight, piston, and superabsorbent particles and record the value on the balance, as DRY WEIGHT in grams to the nearest milligram;
- (5) Gently tap the AUL cylinder until the superabsorbent material is evenly distributed on the bottom of the cylinder;
- (6) Gently place the piston and weight into the cylinder;
- (7) Place the test fluid (0.9 wt. % aqueous sodium chloride solution) in a fluid bath with a large mesh screen on the bottom;
- (8) Simultaneously start the timer and place the superabsorbent particles and cylinder assembly onto the screen in the fluid bath for an hour. The level in the bath should be at a height to provide at least a 1 cm positive head above the base of the cylinder;
- (9) Gently swirl the sample to release any trapped air and ensure the superabsorbent particles are in contact with the fluid.
- (10) Remove the cylinder from the fluid bath at a designated time interval and immediately place the cylinder on the vacuum apparatus (ported disk on the top of the AUL chamber) and remove excess interstitial fluid for 10 seconds;
- (11) Wipe the exterior of the cylinder with paper toweling or tissue;
- (12) Weigh the AUL assembly (i.e., cylinder, piston and weight), with the superabsorbent material and any absorbed test fluid immediately and record the weight as WET WEIGHT in grams to the nearest milligram and the time interval; and The "absorbent capacity" of the superabsorbent particle at a designated time interval is calculated in grams liquid by grams superabsorbent by the following formula:

(Wet Weight−Dry Weight)/(Dry Weight−Container Weight)

Laboratory Screening Procedure

Figure 7:
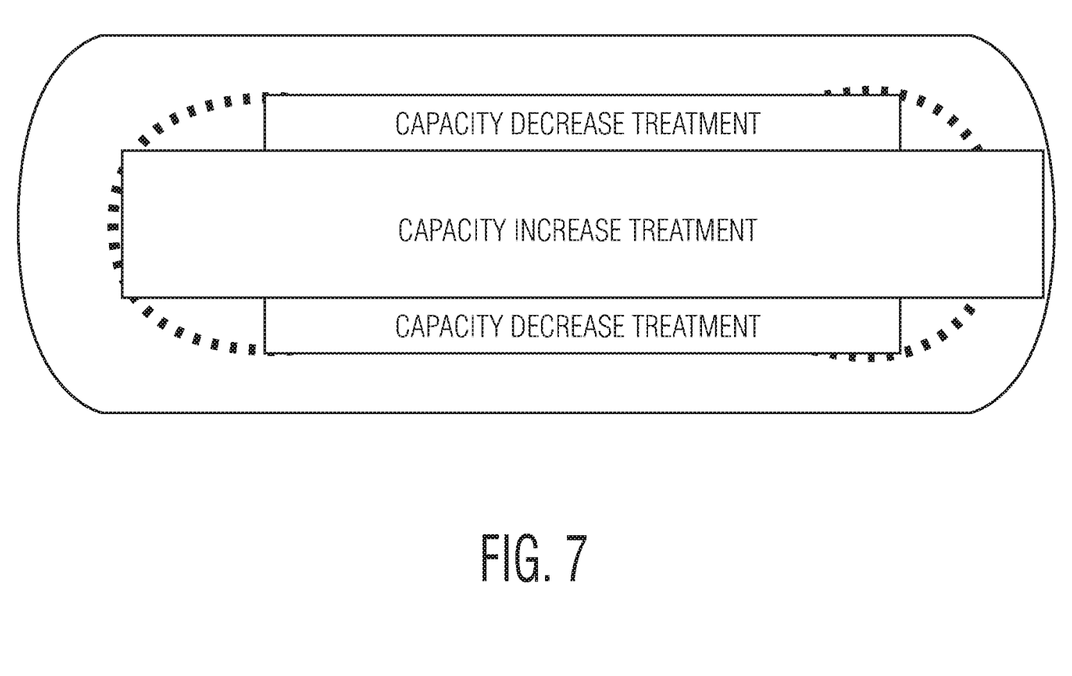
FIG. 7 is a schematic view of a laboratory screening procedure to determine if SAM absorbent capacity may be increased or decreased by treating the SAM with selected MCAs.

To determine if a superabsorbent material (SAM) absorbent capacity may increase or decrease, a laboratory screening procedure was developed. In this procedure (FIG. 7), a desired multifunctional chemical agent (MCA) was first introduced to pre-made SAM in a water solution in an AUL cup and thereafter the AUL testing procedures as described above were followed. The AUL cup was exposed to an excess of 0.9% NaCl under a desired weight to see if the SAM absorbent capacity would increase or decrease in comparison to the control, e.g. the sample with no MCA added.

EXAMPLES

Example 1

Example 1 demonstrates SAM absorbent capacity increases by treating a commercial SAM (i.e. Evonik 5630) with a selected MCA, L-Arginine, in different weight loading levels by following the testing procedures described herein. The results are listed in Table 1.

As shown in Table 1, an increase in SAM absorbent capacity of about 10% may be achieved by treating SAM with the selected MCA, L-Arginine.

TABLE 1

| Evonik SAM 5630 g | L-Arginine g (% SAM Weight) | AUL Capacity (0.6 PSI, 1 hrs) g/g | Capacity Increase (%) |
|---|---|---|---|
| 0.16 | 0 (Control) | 25.33 | 0 (Control) |
| 0.16 | 0.0064 (4%) | 25.97 | 2.53 |
| 0.16 | 0.0128 (8%) | 26.30 | 4.15 |
| 0.16 | 0.0256 (16%) | 27.08 | 6.91 |
| 0.16 | 0.0512 (32%) | 27.87 | 10.03 |

Example 2

Example 2 demonstrates the SAM absorbent capacity increases by treating a commercial SAM (Using Evonik 5630 as example) with a selected MCA, Lysine, in different weight loading levels by following the testing procedures described herein. The results are listed in Table 2.

As shown in Table 2, an increase in SAM absorbent capacity of about 11% may be achieved by treating SAM with the selected MCA, Lysine.

TABLE 2

| Evonik SAM 5630 g | L-Arginine g (% SAM Weight) | AUL Capacity (0.6 PSI, 2 hrs) g/g | Capacity Increase (%) |
|---|---|---|---|
| 0.16 | 0 (Control) | 26.43 | 0 |
| 0.16 | 0.0064 (4%) | 27.06 | 2.38 |
| 0.16 | 0.0128 (8%) | 27.66 | 4.65 |
| 0.16 | 0.0256 (16%) | 28.14 | 6.48 |
| 0.16 | 0.0512 (32%) | 29.46 | 11.46 |

Example 3

Example 3 demonstrates absorbent capacity changes by treating a commercial SAM (i.e. Evonik 5630) with MCA, Glycine, with one amino group in different weight loading levels by following the testing procedures described herein. The results are listed in Table 3.

As shown in Table 3, no significant impact on SAM absorbent capacity was observed by treating SAM with selected MCA, Glycine. Although Glycine has an acid and only one amino group, the formation of an internal zwitterionic structure will significantly limit its ability to either form a complex with the SAM's polymer chain counter ions such as $Na^+$ ions or forming bulky ions through deprotonation by the amino group.

TABLE 3

| Evonik SAM 5630 g | L-Glycine g (% SAM Weight) | AUL Capacity (0.6 PSI, 2 hrs) g/g | Capacity Increase (%) |
|---|---|---|---|
| 0.16 | 0 (Control) | 25.85 | 0 |
| 0.16 | 0.0064 (4%) | 25.86 | ~0 |
| 0.16 | 0.00128 (8%) | 25.90 | ~0 |
| 0.16 | 0.0256 (16%) | 26.18 | ~1.5 |
| 0.16 | 0.0512 (32%) | 26.23 | ~1.5 |

Example 4

Example 4 demonstrates absorbent capacity decreases by treating a commercial SAM (i.e. Evonik 5630) with MCA, Guanidine Sulfate, in different weight loading levels by following the testing procedures described herein. The results are listed in Table 4.

As shown in Table 4, significant absorbent capacity decreases were observed for MCA, Guanidine Sulfate. Guanidine Sulfate has an acid functionality with multiple amino groups on the same carbon. However, the formation of an internal zwitterionic structure significantly reduces its ability to either form a complex with the SAM's polymer chain counter ions such as $Na^+$ ions or form bulky ions through deprotonation by the amino groups.

TABLE 4

| Evonik SAM 5630 g | Guanidine Sulfate g (% SAM Weight) | AUL Capacity (0.6 PSI, 2 hrs) g/g | Capacity Increase (%) |
|---|---|---|---|
| 0.16 | 0 (Control) | 26.18 | 0 |
| 0.16 | 0.0064 (4%) | 25.19 | −3.80 |
| 0.16 | 0.0128 (8%) | 24.64 | −5.89 |
| 0.16 | 0.0256 (16%) | 23.30 | −11.0 |
| 0.16 | 0.0512 (32%) | 21.64 | −17.3 |

Example 5

Example 5 demonstrates the absorbent capacity decreases by treating a commercial SAM (i.e. Evonik 5630) with a selected MCA, Methyl-2-Aminoacetate, in different weight loading levels by following the testing procedures described herein. The results are listed in Table 5.

As shown in Table 5, significant decreases in SAM absorbent capacity were observed by treating SAM with MCA, Methyl-2-Aminoacetate. Methyl-2-Aminoacetate has one amino group but no acid functionality, which does not fit the structural requirements as described in the present invention.

TABLE 5

| Evonik SAM 5630 g | Methyl-2-Aminoacetate g (% SAM Weight) | AUL Capacity (0.6 PSI, 2 hrs) g/g | Capacity Increase (%) |
|---|---|---|---|
| 0.16 | 0 (Control) | 26.16 | Control |
| 0.16 | 0.0064 (4%) | 25.89 | −0.01 |
| 0.16 | 0.0128 (8%) | 25.41 | −2.87 |
| 0.16 | 0.0256 (16%) | 25.32 | −3.20 |
| 0.16 | 0.0512 (32%) | 23.32 | −10.86 |

In summary, the results set forth in Tables 1 and 2 demonstrate surprisingly and unexpectedly that by using the selected MCA structures disclosed herein, SAM absorbent capacity increases.

EMBODIMENTS

First Embodiment: In a first embodiment the invention provides for a method to increase the absorbent capacity of a superabsorbent material (SAM), the method comprising:
providing a superabsorbent material comprising repeated units bearing an anion and a cation wherein the cation is a mono metal ion or a combination of a mono metal ion and a proton ion;
treating the superabsorbent material with a selected multifunctional chemical agent, wherein the selected MCA has structure:

(I)

wherein X is selected from —COOH, —SO$_3$H, and —OSO$_3$H;
wherein N from NR$_1$R$_2$ is selected from a primary, secondary or tertiary amino group and R$_1$ and R$_2$ are selected from —H, -Me, -Et, and -Bu;
wherein R$_3$ is selected from: —H, -Me, -Et, and -Bu;
wherein R$_4$ is an alkyl chain with 8 or less carbons wherein attached to one of the carbons on the alkyl chain comprises at least one or a plurality of primary, secondary or tertiary amino groups further wherein each carbon on the alkyl chain comprises an additional substituent group.

The method according to the preceding embodiment, wherein each additional substituent group on each carbon on the alkyl chain is selected from: —H, -Me, -Et, and -Bu.

The method according to the preceding embodiments, wherein each additional substituent group on each carbon on the alkyl chain is selected from nitrogen-containing alkyl groups.

The method according to the preceding embodiments, wherein the selected multifunctional chemical agent to treat the superabsorbent material is less than 25% of the weight of the superabsorbent material.

The method according to the preceding embodiments, wherein the selected multifunctional chemical agent used to treat the superabsorbent material is incorporated into an absorbent article selected from diapers, training pants, feminine napkins, interlabial pads, tampons, wound management products, and adult incontinence garments.

A superabsorbent material with a multifunctional chemical agent is formed according to the method of the preceding embodiments.

What is claimed is:

1. A method to increase the absorbent capacity of a superabsorbent material, the method comprising:
providing a superabsorbent material comprising repeated units bearing an anion and a cation wherein the cation is a mono metal ion or a combination of a mono metal ion and a proton ion;
treating the superabsorbent material with a selected multifunctional chemical agent, wherein the selected multifunctional chemical agent has a structure:

(I)

wherein X is selected from —COOH, —SO$_3$H, and —OSO$_3$H;
wherein N from R$_1$R$_2$ is selected from a primary, secondary or tertiary amino group and R$_1$ and R$_2$ are selected from —H, -Me, -Et, and -Bu;
wherein R$_3$ is selected from: —H, -Me, -Et, and -Bu;
wherein R$_4$ is an alkyl chain with 8 or less carbons wherein attached to one of the carbons on the alkyl chain comprises at least one or a plurality of primary, secondary or tertiary amino groups further wherein at least one carbon on the alkyl chain comprises an additional substituent group; and
wherein the selected multifunctional chemical agent to treat the superabsorbent material is at least 16% and less than 25% of the weight of the superabsorbent material.

2. The method according to claim 1, wherein each additional substituent group on each carbon on the alkyl chain is selected from: —H, -Me, -Et, and -Bu.

3. The method according to claim 1, wherein each additional substituent group on each carbon on the alkyl chain is selected from nitrogen-containing alkyl groups.

4. The method according to claim 1, wherein the selected multifunctional chemical agent used to treat the superabsorbent material is incorporated into an absorbent article selected from diapers, training pants, feminine napkins, interlabial pads, tampons, wound management products, and adult incontinence garments.

* * * * *